United States Patent
Dick et al.

(10) Patent No.: US 7,703,921 B2
(45) Date of Patent: Apr. 27, 2010

(54) METHOD AND DEVICE FOR TRACKING EYE MOVEMENTS

(75) Inventors: Manfred Dick, Gefell (DE); Joachim Fiedler, Crailsheim (DE)

(73) Assignee: Carl Zeiss Meditec AG, Jena (DE)

( * ) Notice: Subject to any disclaimer, the term of this patent is extended or adjusted under 35 U.S.C. 154(b) by 1879 days.

(21) Appl. No.: 10/482,886

(22) PCT Filed: Jul. 8, 2002

(86) PCT No.: PCT/EP02/07591

§ 371 (c)(1),
(2), (4) Date: Jan. 5, 2004

(87) PCT Pub. No.: WO03/003909

PCT Pub. Date: Jan. 16, 2003

(65) Prior Publication Data

US 2004/0189939 A1   Sep. 30, 2004

(30) Foreign Application Priority Data

Jul. 6, 2001 (DE) .................. 101 32 378

(51) Int. Cl.
*A61B 3/14* (2006.01)
*A61B 3/10* (2006.01)
*A61B 3/00* (2006.01)

(52) U.S. Cl. .................. 351/209; 351/205; 351/246

(58) Field of Classification Search .................. 351/205, 351/209–210, 246
See application file for complete search history.

(56) References Cited

U.S. PATENT DOCUMENTS

| 5,818,954 A | 10/1998 | Tomono et al. |
| 5,861,936 A * | 1/1999 | Sorensen ................. 351/200 |
| 5,980,513 A | 11/1999 | Frey et al. ................. 606/10 |
| 6,325,512 B1 * | 12/2001 | Wei ................. 351/209 |
| 6,607,527 B1 * | 8/2003 | Ruiz et al. ................. 606/41 |

FOREIGN PATENT DOCUMENTS

| DE | 19702335 | 8/1998 |
| DE | 19926476 | 12/2000 |
| EP | 0850614 | 7/1998 |
| JP | 10192334 | 7/1998 |
| WO | 9965381 | 12/1999 |
| WO | WO-9965381 | 12/1999 |
| WO | 0027273 | 5/2000 |
| WO | WO-0027273 | 5/2000 |
| WO | WO-0189438 | 11/2001 |

OTHER PUBLICATIONS

Telfair et al., 'Scanning mid-IR laser apparatus with eye tracking for refractive surgery', in SPIE vol. 3591, Jan. 1999, pp. 220-228.

* cited by examiner

*Primary Examiner*—Scott J Sugarman
*Assistant Examiner*—Dawayne A Pinkney
(74) *Attorney, Agent, or Firm*—Darby & Darby

(57) ABSTRACT

A method and a device for tracking eye movements that ensure a reliable tracking of eye movements with simple operation. To this end, irradiation ensues through the pupil from outside the eye. Light emitted from the pupil is used to determine the position of the eye.

26 Claims, 2 Drawing Sheets

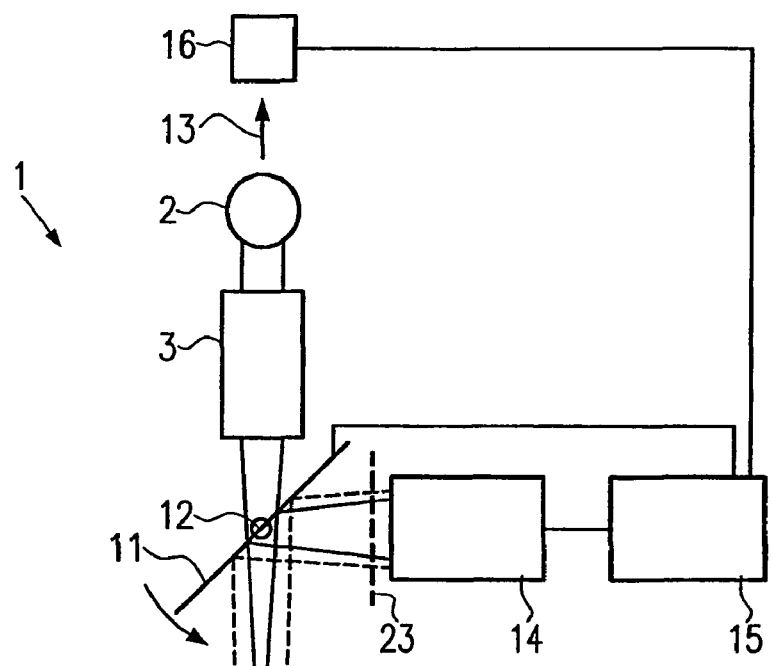
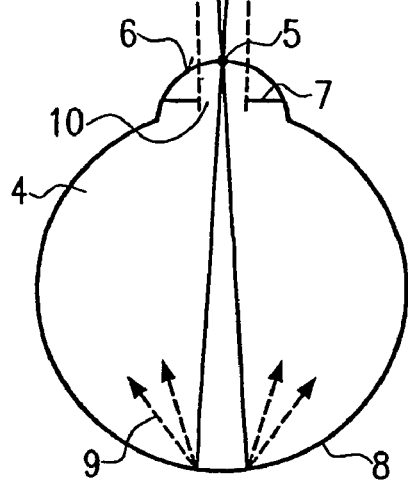
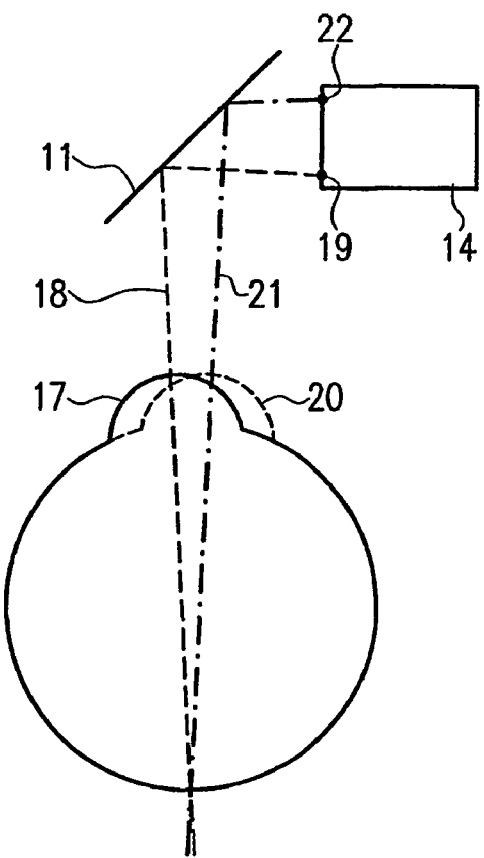
FIG. 1.A
FIG. 2

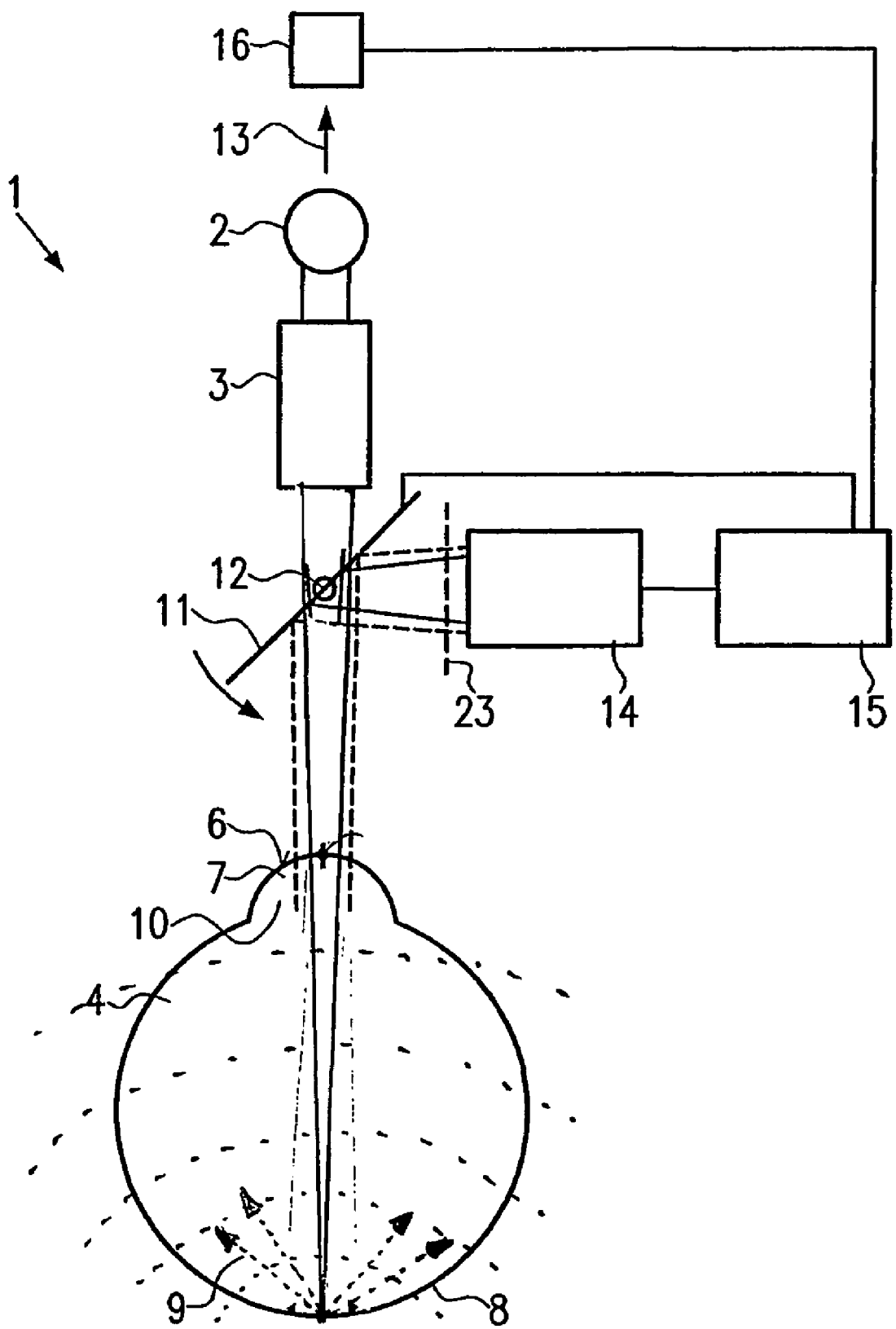
Fig. 1.B

METHOD AND DEVICE FOR TRACKING EYE MOVEMENTS

BACKGROUND

The present invention relates to a method and a device for tracking eye movements.

Refractive laser surgery of the cornea, in particular with ablative excimer lasers (ArF—wavelength 193 nm) as OP laser, has become an established method of treating refractive sight defects. The treatment is carried out with so-called spot scanning systems on the patient's freely-moving eye. These systems also allow patient-specific corrections, so-called customized ablations.

A patient's eye movement makes it necessary to guide the beam of the OP laser in line with the movement. To this end the patient's eye movement and thus the current eye position is recorded with a so-called eye-tracking system and used as adjustment value to steer the OP laser. Customary eye-tracking systems work on the basis of image-processing systems in which these can for example measure the pupil of the eye using a digital camera and determine the eye position with image-processing algorithms by comparing image sequences. As eye movements take place very rapidly and as even the smallest angle errors have to be recognized, high-speed video cameras are normally used for this purpose.

The pupil is preferably used as tracking object for the high-speed video camera, as an automatic video-supported pupil centering can thereby be carried out at the start and the same object can also be tracked during the treatment. This procedure is problem-free on an untreated eye. However, already during preparatory operations such as the removal of the epithelium during PRK (photorefractive keratectomy) or lifting up the flap during LASIK (laser-assisted in-situ keratomileusis), the contrast ratios are changed. During the laser treatment this problem is further aggravated, as a strongly dispersive surface beyond the diameter of the pupil is created.

To avoid this problem different optimization approaches have been worked out. There is a switch to other tracking objects on the eye such as e.g. limbus or iris after initial pupil centering or additional tracking rings are placed on the eye in order to ensure a stable functioning of the eye tracking during the treatment. However, this entails unwelcome additional treatment costs.

In another optimization approach the eye is illuminated from the side with infrared LEDs. A lower failure rate of the system is thereby also achieved during the laser treatment.

However, the illumination necessitates additional work for the doctor and a limitation of working freedom in the OP field.

SUMMARY OF THE INVENTION

An object of the present invention is to provide a method and a device for tracking eye movements which ensure a reliable tracking of the eye movement while being as simple to use.

The method according to the invention provides that the irradiation takes place through the pupil or the pupil forms a quasi-monochromatic IR source through the reflected light.

In a further embodiment of the method it is provided that the excitation of the inside of the eye for illumination takes place through a light source arranged coaxial to the optical axis of an OP laser. This method has the advantage that the operating doctor need only handle a single radiation source.

In a further embodiment of the method it is provided that the light source is an IR laser diode. In this way an adequate light intensity can be achieved without disruptive light reflexes for example for the operating doctor.

In a further embodiment of the method it is provided that the IR laser diode operates pulsewise. This allows a high instant-radiation output with a correspondingly high brightness of the reflected light with a comparatively low average irradiation output.

In a further embodiment of the method it is provided that the pulses of the IR laser diode are synchronized with the laser-firing frequency of the OP laser such that the IR laser diode illuminates only in laser firing pauses of the OP laser. This measure reduces possible interferences with or impairments of the camera lens by the OP laser used.

In a further embodiment of the method it is provided that the pulses of the IR laser diode are synchronized with the image frequency of a camera which absorbs the light emitted by the eye. The camera therefore only records images which are generated by the IR laser diode during irradiation of the eye. This measure further reduces inaccuracies caused by images produced by the OP laser.

In a further embodiment of the method it is provided that the radiation of the laser diode has a focal point on the surface of the cornea of the eye. In this way the best use is made of the optical properties of the eye itself.

In a further embodiment of the method it is provided that the radiation of the laser diode has a spot which is broadened as much possible on the retina of the eye. This measure optimizes the intensity of the back-scattered light.

The present invention also provides a device for tracking eye movements, in particular during refractive laser surgery, comprising a light source configured to irradiate an inside of the eye through the pupil so as to excite the inside of the eye to illumination, a camera configured to detect light emitted from the pupil, and an evaluation unit operatively connected to the camera and configured to determine a position of the eye. In a preferred version it is provided that the radiation of the light source and the light reflected from the eye run essentially coaxial. In this way all the elements to be used during the refractive laser surgery of the eye can be grouped in a single housing and thus only one device is to be operated by the doctor.

In a further embodiment of the device it is provided that the radiation of the light source and the light reflected from the eye run essentially coaxial. This measure makes it possible to further combine the components in only one housing unit.

In a further embodiment of the device it is provided that the reflected light is guided by a scanner mirror onto the camera arranged non-coaxial relative to the radiation of the illuminating unit. Using the scanner mirror, the two beam paths can thus be split well away from the eye.

The scanner mirror is preferably designed such that it admits most of the light striking it from the light source and the eye is thus irradiated and the light reflected from the eye is reflected. Mirrors can also be optimized with dielectric coating only for transmission or reflection. Because of the lesser light intensity reflected by the eye and the possibility of choosing virtually any light source output, the scanner mirror is optimized for the reflection in the present application.

In a further embodiment of the device it is provided that a filter is arranged in the beam path of the reflected light which essentially passes light of the wavelength emitted from the light source. Perturbing radiation which strikes the eye from the surrounding area and is reflected by the former can thus be filtered out. The intensity of the light irradiated from the light source onto the eye cannot be increased at will out of consideration for the load-bearing capacity of the retina of the eye. An improvement of the perturbing radiation distance is therefore effected here by filtering out the interference spectrum. This measure increases the contrast ratio between pupil and surrounding area.

A dielectric filter element is preferably used with which the surrounding intensity is strongly suppressed because of the monochromatism of the laser radiation and thus a good contrast ratio can be produced.

In a further preferred embodiment of the present invention a point of fixation on the cornea is chosen to determine the eye position. The purpose of such a point of fixation is to enable the eye movement to be tracked and to ascertain an "offset" for the current coordinates of the eye with reference to this point. The firing parameters and coordinates can then for example be ascertained by way of deviation from this point.

This point of fixation is particularly preferably the geometric centre of the optical image of the pupil. This geometric centre or centre of gravity of the pupil is then taken as point of fixation. Since the diameter of the pupil changes, this centre shifts over time. This centre or point of fixation is preferably regularly redetermined. Thus the point of fixation is kept on the cornea. The "offset" which can for example be transmitted to a scanner mirror is then determined from the allocation of this point of fixation.

In a further preferred embodiment of the present invention the lateral displacement of the eye or the rolling movement of the eye is recorded by evaluating the image of the pupil. Spherical objects, such as for example the eye, can thereby be treated with lasers, account being able to be taken of whether the ablation spot of the laser is directed towards the centre of the ball or the eye, or the laser firing, in its notional extension, passes well away from the centre of the eye or the ball. The efficiency of the ablation spot of the laser depends on this. If this strikes the ball surface peripherally on the edge, i.e. the notional extended laser firing passes by the centre of the eye, then a higher energy must be expended for the same ablation effect, as the laser spot then strikes the ball or surface of the eye as an elliptical projection of the circular spot. If the firing is targeted precisely on the centre of the ball or the eye, the efficiency of the laser spot is then at its highest in the ablation. By taking into account the rolling movement of the eye as well as the translatory or lateral displacement, these energy effects can be equalized and precisely taken into account in each case in consideration of the optimum efficiency using the position of the eye and of the ablation spot to be applied. Thus an even more accurate treatment of the surface is possible. The unrolling or rolling of the eye can be ascertained by image processing, in particular via the evaluation of the recorded structure of the iris. The anterior chamber depth of the eye is preferably also taken into account. The angle of rotation of the eye can then be ascertained and this effect thus also taken into account with regard to the energy input on the ball surface outside the centre.

In a further preferred method of the present invention a compensation factor is calculated from an average eye length and an average anterior chamber depth, which corresponds to the parallax between the cornea front surface and entrance pupil. The deviations which can result from the rolling movement of the eye can thereby be compensated. An average value for the biometric parameters such as eye length and anterior chamber depth is preferably used here. Time-consuming pre-measurements can therefore be avoided, which leads to a swifter implementation of the method.

The compensation factor is preferably transmitted onto scanner mirrors of a working laser. The values obtained to compensate for the parallax can be directly transmitted onto the scanner mirrors which deflect a working laser beam and thus ensure that the parallax can be directly compensated for on the ball surface to be treated.

The compensation factor may be linear. For small angles in this geometrically measured parallax for example the approximation is true that the sine can be replaced by the argument. In addition, further approximation possibilities exist which allow a simple determination of this compensation factor. This linear (approximated) compensation factor can be easily and quickly measured and thus allows a swift implementation of the method according to the invention.

The compensation factor particularly preferably obeys a non-linear function. This non-linear function for establishing the compensation factor is the geometrically correct function, while the linear relationship represents an approximation. It is precisely for larger angles in the parallax that the approximations can lead to undesired deviations or errors. Greater deviations can thus be better compensated with the preferred method.

The compensation factor is preferably determined by the individual measurement of biometric parameters. Such biometric parameters are in particular the eye length and/or the anterior chamber depth. The eye length is particularly preferably individually determined as it is easy to measure. The anterior chamber depth is (also) quite particularly preferably individually determined as a particularly correct compensation can be individually carried out using same.

BRIEF DESCRIIPTION OF THE DRAWINGS

Further advantageous designs of the invention will be explained in the following using the drawings. There are shown in FIG. 1a a schematic diagram of the structure of the device;

FIG. 1b a schematic diagram of the structure of a further embodiment of the device according to the invention;

FIG. 2 a schematic diagram of the beam path of the device.

DETAILED DESCRIPTION

A device for tracking the eye movement 1 includes a light source 2, and a telescope 3. The light emitted from the light source 2 is guided via the telescope 3, which can be equipped with further optical apparatuses, for example such as lenses or similar, to an eye 4 of a person to be treated, not shown. The light is concentrated in a focal point 5. The focal point 5 lies on the cornea surface 6 of the iris 7 of the eye 4. After passing through the cornea surface 6 the light beam of the light source 2 broadens and strikes the retina 8 of the eye 4 as a broadened spot. The light source 2 is an infrared laser diode in the present embodiment. Its output is chosen such that the permissible irradiation intensity for the retina 8 is observed.

The light striking the retina 8 is diffusely reflected by same, as indicated by the arrow 9 in FIG. 1. The light 9 reflected from the retina 8 leads to a homogenous illumination of the pupil 10.

After the reflected light 9 has passed through the pupil 10, it strikes a scanner mirror 11. This is movable about at least two axes, for example about the lateral axis 12 projecting from the plane of the drawing and the vertical axis given the reference number 13 in FIG. 1. Through movement about these two axes the scanner mirror 11 can project different areas of the retina 8 of the eye 4 onto a camera 14. The camera 14 is connected to an evaluation unit 15 which controls the scanner mirror 11 on the one hand and an OP laser 16, not shown in more detail, on the other. The optical axis of the OP laser 16 is arranged coaxial to the optical axis of the device for eye tracking 1.

The scanner mirror 11 is designed such that it passes only a small part of the light, for example roughly 2%, and reflects the greater part of the light, for example roughly 98%. Alternatively, the scanner mirror 11 can be provided with a small hole, or the camera 14 can observe the eye 4 in the non-coaxial beam path.

The infrared laser diode of the light source 2 is operated pulsewise. The light pulses are synchronized, using the evaluation unit 15, with the laser firing frequency of the OP laser 16. The resultant pulsewise illumination by the IR laser diode minimizes the loading of the retina 8 and increases the contrast between illuminated and non-illuminated areas.

The infrared laser diode of the light source 2 emits a monochromatic light. The light reflected from the eye has the same wavelength as the light emitted by the infrared laser diode. This wavelength is filtered out for example by a dielectric filter. Other wavelengths which for example radiate from the surrounding area onto the eye and are reflected by this or strike the camera directly are thereby filtered out. The contrast between illuminated and non-illuminated areas or the pupil and its surrounding area can thereby be further increased.

A further embodiment of the invention is shown in FIG. 1B. The structure corresponds to that of the device from FIG. 1A. Here, the focal point of the beam is directed not onto the pupil but directly onto the retina. The focal point of the IR source on the retina now generates fluorescence. A homogenous illumination of the pupil is achieved by spherical waves (indicated by a dotted line), which are now reflected by the retina. This leads to a preferred regredient illumination. The retina itself can then function as a light source and not as a light trap.

FIG. 2 illustrates the determination of the eye movement or the eye position using two examples of the eye position. In a first eye position 17, represented by a solid line of the iris 7, a first light beam 18 is guided via the scanner mirror 12 onto a first imaging point 19 of the camera 14. By moving the scanner mirror 11 about its lateral axis 12 and its vertical axis 13 a complete image of an area of the retina 8 can thus be produced on the camera 14.

When the eye position changes to a second eye position 20, the same point of the retina 8 then produces a second light beam 21 which strike the camera 14 in a second imaging point 22. When the scanner mirror 11 is moved as previously described an image of an area of the retina 8 is likewise produced on the camera. This imaging of the retina 8 is shifted vis-a-vis the first eye position 17 on the camera 14. By carrying out a suitable mathematical comparison of the digitalized images of the camera 14 by means of the evaluation unit 15, the changed angular position of the eye 4 can thus be deduced. The point-focal reflex or scatter point that results on the cornea surface 6 is masked off by the image-processing video system of the evaluation unit 15.

What is claimed is:

1. A method for tracking eye movements of an eye having a cornea and a pupil, the method comprising:
    irradiating an inside of the eye through the pupil from outside of the eye so as to excite the inside of the eye to homogeneously illuminate the pupil, wherein the irradiation has a focal point directed onto the cornea of the eye; and
    determining a position of the eye using light emitted from the homogeneously illuminated pupil.

2. The method as recited in claim 1 wherein the irradiating is performed using a light source disposed coaxially with an optical axis of an OP laser.

3. The method as recited in claim 2 wherein the light source is an IR laser diode.

4. The method as recited in claim 3 wherein the IR laser diode operates using pulses.

5. The method as recited in claim 4 wherein the IR laser synchronizes the pulses with a laser firing frequency of the OP laser such that the IR laser diode illuminates only in laser firing pauses of the OP laser.

6. The method as recited in claim 4 further comprising absorbing the light emitted from the pupil using a camera and wherein the IR laser diode synchronizes the pulses with an image frequency of the camera.

7. The method as recited in claim 1 wherein the irradiating is performed using a laser diode.

8. The method as recited in claim 1 wherein the irradiating is performed using a laser diode projecting a spot on the retina of the eye.

9. The method as recited in claim 8 wherein the spot is projected to be as broad as possible.

10. The method as recited in claim 1 wherein the eye position is determined by determining a point of fixation on the cornea.

11. The method as recited in claim 10 wherein the point of fixation is a geometric center of an optical image of the pupil.

12. The method as recited in claim 10 further comprising regularly redetermining the point of fixation.

13. The method as recited in claim 1 further comprising detecting at least one of a lateral shift of the eye and a rolling movement of the eye by evaluating an image of the pupil.

14. The method as recited in claim 1 wherein further comprising calculating a compensation factor using an average eye length and an average anterior chamber depth, the compensation factor corresponding to a parallax between a front surface of a cornea and entrance pupil.

15. The method as recited in claim 14 further comprising transmitting the compensation factor to scanner mirrors of a working laser.

16. The method as recited in claim 14 wherein the compensation factor obeys a linear function.

17. The method as recited in claim 14 wherein the compensation factor obeys a non-linear function.

18. The method as recited in claim 14 wherein the calculating of the compensation factor is performed by individual measurement of at least one biometric parameter.

19. The method as recited in claim 1 wherein the method is performed during refractive laser surgery.

20. A device for tracking eye movements of an eye having a cornea and a pupil, comprising:
    a light source configured to irradiate an inside of the eye through the pupil so as to excite the inside of the eye to homogeneously illuminate the pupil, wherein the irradiation has a focal point directed onto the cornea of the eye;
    a camera configured to detect light emitted from the homogeneously illuminated pupil;
    an evaluation unit operatively connected to the camera and configured to determine a position of the eye.

21. The device as recited in claim 20, wherein the light source is positioned so that a radiation from the light source and a light reflected from the eye run along a same axis.

22. The device as recited in claim 21, further comprising a scanner mirror positioned on the axis and configured to guide the light reflected from the eye onto the camera, and wherein the camera is not arranged along the axis.

23. The device as recited in claim 22, wherein light from the light source passes through the scanner mirror.

24. The device as recited in claim 20 wherein the light source emits light having a wavelength and further comprising a filter disposed in a beam path of the reflected light, the filter configured to admit light having the wavelength.

25. The device as recited in claim 24, wherein the filter includes a dielectric filter element.

26. The device as recited in claim 20, wherein the light source irradiates the inside of the eye during refractive laser surgery.

* * * * *